United States Patent [19]
Kennedy et al.

[11] Patent Number: 5,961,980
[45] Date of Patent: *Oct. 5, 1999

[54] BOWMAN-BIRK INHIBITOR COMPOSITIONS AND METHODS FOR THE TREATMENT OF GENITOURINARY DISEASES

[75] Inventors: Ann R. Kennedy, Wynnewood, Pa.; Larry Clark, Tucson, Ariz.

[73] Assignee: The Trustees of the University of Pennsylvania, Philadelphia, Pa.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/588,462

[22] Filed: Jan. 18, 1996

[51] Int. Cl.$^6$ .................................................. A61K 35/78
[52] U.S. Cl. .......................................................... 424/195.1
[58] Field of Search ........................ 424/195.1; 435/69.2, 435/213

[56] References Cited

U.S. PATENT DOCUMENTS

| | | | |
|---|---|---|---|
| 4,793,996 | 12/1988 | Kennedy et al. | 424/195.1 |
| 5,217,717 | 6/1993 | Kennedy et al. | 424/195.1 |
| 5,505,946 | 4/1996 | Kennedy et al. | 424/195.1 |
| 5,550,042 | 8/1996 | Sambrook et al. | 435/172.1 |

OTHER PUBLICATIONS

Baturay et al., "Pyrene Acts as a Cocarcinogen with the Carcinogens Benzo [A] Pyrene, β–Propiolactone and Radiation in the Induction of Malignant Transformation in Cultured Mouse Fibroblasts; Soybean Extract Containing the Bowman–Birk Inhibitor Acts as an Antocarcinogen".
Birk et al., "Separation of a Tribolium–protease inhibitor from soybeans on a calcium phosphate column", *Biochim. Biophys. Acta* 1963, 67,326.
Bowman,D.E., "Differentiation of Soy Bean Antityptic Factors", *Proc. Soc. Exptl. Med.* 1946, 63, 547.
Evans et al., "Protection against Metastasis of Radiation–Induced Thymic Lymphosarcoma and Weight Loss in C57B1/6NCr1BR Mice by an Autoclave–Resistant Factor Present in Soybeans", *Radiat. Res.* 1992,132, 259–262.
Frenkel et al., "Chymotrypsin–specific protease inhibitors decrease $H^2O^2$ formation by activated human polymorphonuclear leukocytes",*Carcinogenesis* 1987, 8(9), 1207–1212.
Gibas et al., "A High–Resolution Study of Chromosome Changes in a Human Prostatic Carcinoma Cell Line (LNCaP)", *Cancer Genet. Cytogen.* 1984, 11, 399–404.
Horoszewicz et al., "LNCaP Model of Human Prostatic Carcinoma", *Cancer Res.* 1983, 43, 1809–1818.
Kaighn et al., Establishment and Characterization of a Human Prostatic Carcinoma Cell Line (PC–3), *Invest. Urol.* 1979, 17, 16–23.

Kennedy, "Cancer Prevention by Protease Inhibitors", *Prevent. Med.* 1993, 22, 796–811, pp. 797.
Kennedy, "The Evidence for Soybean Products as Cancer Preventive Agents", *J. Nutr.* 1995, 125, 733S–743S.
Messadi et al., "Inhibition of Oral Carcinogenesis by a Protease Inhibitor", *JNCI* 1986, 76, 447–452.
Muschel et al., "Induction of Apoptosis at Different Oxygen Tensions: Evidence That Oxygen Radicals Do Not Mediate Apoptotic Signaling", *Cancer Res.* 1995, 55, 995–998.
Ohnuki et al., "Chromosomal Analysis of Human Prostatic Adenocarcinoma Cell Lines", *Cancer Res.* 1989, 40, 524–534.
Perlmann et al., "Proteolytic Enzymes", *Methods in Enzymology* 1970, 19, 860–861.
Samid et al., "Selective Growth Arrest and Phenotypic Reversion of Prostate Cancer Cells In Vitro by Nontoxic Pharmacological Concentrations of Phenylacetate", *J. Clin Invest.* 1993, 91, 2288–2295.
St. Clair et al., "Suppression of Dimethylhydrazine–induced Carcinogenesis in Mice by Dietary Addition of the Bowman–Birk Protease Inhibitor", *Cancer Res.* 1990, 50, 580–586.
von Hofe et al., "Inhibition of N–nitrosomethylbenzylamine–induced esophageal neoplasms by the Bowman–Birm protease inhibitor", *Carcinogenesis* 1991, 12, 2147–2150.
Vindelov and Christensen, "A Review of Techniques and Results Obtained in One Laboratory by an Integrated System of Methods Designed for Routine Clinical Flow Cytometric DNA Analysis", *Cytometry* 1990, 11, 753–770.
Ware et al., "Spontaneous Metastasis of Cells of the Human Prostate Carcinoma Cell Line PC–3 in Athymic Nude Mice", *J. Urol.* 1982, 128, 1064–1067.
Weed et al., "Protection against dimethylhydrazine–induced adenomatous tumors of the mouse colon by the dietary addition of an extract of soybeans containing the Bowman–Birk protease inhibitor", *Carcinogenesis* 1985, 6, 1239–1241.
Yavelow et al., "Bowman–Birk Soybean Protease Inhibitor as an Anticarcinogen", *Cancer Res.* 1983, 43, 2454–2459.
Yavelow et al., "Nanomolar concentrations of Bowman–Birk soybean protease inhibitor suppress x–ray–induced transformation in vitro", *Proc. Natl. Acad. Sci. USA* 1985, 82, 5395–5399.
Kennedy A., The Evidence for Soybean Products as Cancer Prventive Agents, J Nutr 125:733S–743S, 1995.

*Primary Examiner*—Ralph Gitomer
*Attorney, Agent, or Firm*—Law Offices of Jane Massey Licata

[57] ABSTRACT

A composition containing a Bowman Birk Inhibitor and a pharmaceutically acceptable carrier are provided for treatment of genitourinary tract diseases relating to smooth muscle contraction leading to urinary symptoms and male sexual dysfunction or atypical prostate cells. Methods of using these compositions in treatment of these diseases are also provided.

1 Claim, 3 Drawing Sheets

BOWMAN-BIRK INHIBITOR COMPOSITIONS AND METHODS FOR THE TREATMENT OF GENITOURINARY DISEASES

BACKGROUND OF THE INVENTION

This invention relates to a composition and method for the alleviation of disease symptoms and the treatment of abnormal conditions occurring in the pelvic region related to smooth muscle contractions involving male sexual dysfunction and urinary symptoms, inflammation and treatment of several common diseases of the prostate including prostatitis, benign prostatic hyperplasia and adenocarcinoma of the prostate. The symptoms covered by this invention are all related to medical problems associated with the genitourinary tract. About half of the male population experience symptoms of prostatic inflammation during adult life. Benign prostatic hyperplasia (BPH) is a disease which is related to aging and associated changes in circulating hormones. As the hyperplastic prostate enlarges, it compresses the urethra and may cause incomplete emptying of the bladder. The most common treatment for BPH is surgery. Balloon dilation or drug therapy using $\alpha 1$ blockers such as terazosin and prazosin is used in some cases. Antiandrogen therapy may also relieve prostatic obstruction.

Carcinoma of the prostate is a significant cause of death in men over 55 years of age. The etiology of prostatic carcinoma is unknown. Early carcinoma of the prostate is asymptomatic. As the disease spreads, it may cause urinary obstruction. Determination of serum acid phosphatase is a basic screening test for metastatic prostate cancer. Elevation of serum prostate-specific antigen (PSA) level in the serum is the most sensitive test for early detection of prostatic cancer. The serum PSA level may be elevated with localized disease, while elevation of acid phosphatase level usually indicates extra-prostatic disease. Following diagnosis and treatment, serial determinations of serum PSA levels are done for assessing response. Treatment includes surgery, radiation and hormonal therapy. Cytotoxic chemotherapy has so far not proven effective.

Protease inhibitors are classes of compounds commonly found in many different types of foods, such as legumes, cereals, nuts, fruits and vegetables. One of the best characterized protease inhibitors is the Bowman-Birk Inhibitor (BBI) which is derived from soybeans. It is a 71 amino acid chain with 7 disulfide bonds that binds 1:1 with trypsin and chymotrypsin at different binding sites and has a molecular weight of approximately 8000.

In vivo and in vitro studies of protease inhibitors, and BBI in particular, have shown them to be effective anticarcinogenic agents. It has been shown that the enzyme-inhibitor described by Bowman, *Proc. Soc. Exptl. Med.* 1946, 63, 547 and Birk et al., *Bull. Res. Council Israel* 1962, Sec. 1, 11, 48 and *Biochim. Biophys. Acta* 1963, 67, 326, and subsequently referred to as the Bowman-Birk Inhibitor (BBI), possesses certain physiological activity that prevents, or at least greatly reduces, radiologically or chemically induced malignant transformation of cells in culture and in experimental animals.

Yavelow et al., *Proc. Natl. Acad. Sci. USA* 1985, 82, 5395–5399, reported that a crude soybean extract, if defatted with acetone, effectively blocked cell transformation in vitro. These observations, with epidemiological data, suggested BBI as a putative dietary anticarcinogen, particularly with respect to colon cancer.

Weed et al., *Carcinogenesis* 1985, 6, 1239–1241, disclose that an extract of soybeans containing the Bowman-Birk protease inhibitor added to the diet of dimethylhydrazine (DMH)-treated mice resulted in a significant suppression of adenomatous tumors of the colonic mucosa. DMH-induced colon cancer in mice is generally regarded as an excellent animal model for the human disease, with carcinogen treatment inducing adenocarcinomas of the colon and rectum which are similar to the tumors arising in the human colon suggesting the possibility that a dietary additive of the sort studied might confer some protection against the development of human colon cancer without undesirable side effects. The BBI extract and methods for its preparation were as described by Yavelow et al., *Cancer Res.* 1983, 43, 2454–2459; *Proc. Natl. Acad. Sci. USA* 1985, 82, 5395–5399.

Messadi et al., *JNCI* 1986, 76, 447–452 demonstrated that a soybean extract containing the protease inhibitor BBI suppresses 7,12-dimethyl-benz[a]anthracene (DMBA)-induced carcinogenesis in the hamster cheek pouch. This oral cancer model has the same histopathology, growth pattern and precancerous lesions as the most common form of human oral cancer, squamous cell carcinoma. It was shown in this study that hamster cheek pouch carcinogenesis can be inhibited by BBI and suggested that human oral carcinogenesis might respond to BBI in a comparable manner. The BBI preparation used in this study was a crude extract of the inhibitor prepared as described by Yavelow et al., *Proc. Natl. Acad. Sci. USA* 1985, 82, 5395–5399.

Baturay et al., *Cell Biology and Toxicology* 1986, 2, 21–32 disclose that a BBI preparation, wherein a crude soybean extract is defatted with acetone, suppresses radiation and chemically induced transformation in vitro, with or without enhancement by the co-carcinogen, pyrene. Yavelow et al., 1985, show that either pure BBI or the BBI extract prepared in accordance with their methods suppresses radiation induced transformation in C3H10T1/2 cells. Kennedy et al., 1984, report that either pure BBI or the BBI extract prepared in accordance with their method reduce the levels of chromosome abnormalities in cells of patients with Bloom's syndrome (a genetic disease in which the high levels of chromosome abnormalities are thought to predispose the patients to a higher than normal cancer incidence). Still, other studies suggest that soybean-derived protease inhibitors can have suppressive effects on skin, breast and liver carcinogenesis in vivo.

Kennedy et al. in *Anticarcinogenesis and Radiation Protection*, edited by Cerutti et al., Plenum Pub. Co. 1987, pp. 285–295, disclose that BBI suppresses carcinogenesis in various systems using a crude BBI extract prepared by defatting soybeans with acetone. Their results suggested that very low concentrations of BBI-type protease inhibitor preparations would be effective as chemopreventive agents for colon cancer. There was no evidence to suggest that the use of protease inhibitors as chemopreventive agents would be complicated by possible toxicity problems.

St. Clair et al., *Cancer Res.* 1990, 50, 580–586, report that the addition of 0.5% or 0.1% semi-purified BBI to the diet of DMH-treated mice resulted in a statistically significant suppression of angiosarcomas and nodular hyperplasia of the liver and colon carcinogenesis. The results of this study also indicate that BBI, included as 0.5% of the diet or less, had no adverse effect upon the health of the mice but had the capacity to suppress liver and colon carcinogenesis.

A soybean extract enriched in BBI, termed Bowman-Birk inhibitor concentrate (BBIC), has achieved Investigational New Drug Status from the Food and Drug Administration and human trials to evaluate it as a human cancer chemotherapeutic agent have begun.

Frenkel et al. *Carcinogenesis* 1987, 8(9), 1207–1212 monitored formation of $H_2O_2$ by 12-O-tetradenoyl-phorbol-13-acetate (TPA)-activated polymorphonuclear leukocytes (PMNs) in the absence or presence of protease inhibitors and/or superoxide dismutase (SOD). Protease inhibitors tested include potato inhibitors 1 (PtI-1) and 2 (PtI-2), a chymotrypsin inhibitory fragment of PtI-2 (PCI-2), chicken ovoinhibitor (COI), turkey ovomucoid ovoinhibitor (TOOI), Bowman-Birk inhibitor (BBI), lima bean inhibitor (LBI) and soybean (Kunitz) trypsin inhibitor (SPTI). The order of activity, as measured by inhibition of $H_2O_2$ formation, was PtI-1≧PCI-2>PtI-2>COI>BBI≧TOOI>LBI>SBTI thus showing that protease inhibitors specific for chymotrypsin, but not those that are trypsin-specific, are capable of inhibiting formation of active oxygen species during the oxidative burst of stimulated human PMNs. BBI was characterized as an inhibitor of both chymotrypsin and trypsin.

Perlmann et al., *Methods in Enzymology* 1970, 19, 860–861, have described an elaborate method for obtaining BBI from a defatted soybean extract.

U.S. Pat. No. 4,793,996 (Kennedy et al.) discloses a process comprising treating soybeans with acetone, followed by ethanol extraction and acetone precipitation for obtaining BBI. The soybeans may be defatted prior to acetone treatment. In addition, BBI may be further purified by conventional techniques. Kennedy et al. discovered that in the conventional process for preparing BBI from soybeans, a factor remained which adversely affected the ability of BBI to inhibit the malignant transformation of cells. If the factor was removed, the resulting BBI product was capable of inhibiting the malignant transformation of cells. It was found to be possible to remove this factor by treating the soybeans with acetone prior to the ethanol extraction step taught by Perlmann et al.

Kennedy et al. teach that it is unnecessary to carry out a procedure requiring complete purification of the extract to the point where the product contains only a single protein. Instead, they found it effective to stop the purification procedure at a point where a crude inhibitor extract is obtained. This crude extract is itself edible and can be used as an inhibitor of malignant transformation of cells, for example, by oral ingestion. Kennedy et al. disclose a process for preparing a crude soybean extract containing an inhibitor of malignant cell transformation which comprises defatting soybeans and extracting said inhibitor from said defatted soybeans.

SUMMARY OF THE INVENTION

An object of the present invention is to provide a BBI composition for the treatment of several abnormal conditions occurring in the genitourinary tract/pelvic region related to smooth muscle contractions leading to urinary symptoms and male sexual dysfunction, as well as a treatment for several diseases of the prostate.

Another object of the present invention is to provide a method for treating such conditions and diseases comprising administering an effective amount of BBI to an animal having the condition or disease.

DETAILED DESCRIPTION OF THE INVENTION

Prostate cancer is a major cause of mortality and the second most common cancer in the United States male population. The incidence of prostate cancer has increased approximately 50% during the past decade; in 1994, 200,000 new cases of prostate cancer were diagnosed and 38,000 people died from prostate cancer in the United States. Prostate cancer can be treated with radical prostatectomy or radiotherapy; however, many prostate cancer patients can not be cured. It has been reported that less than 40% of patients with advanced prostate cancer (designated as T1-2Nx tumor) can be cured by conventional radiation therapy and that the cure rate drops further, to less than 20% for patients with a more advanced stage of prostate cancer (designated as T3-4Nx tumor). Most recurrence of prostate cancer involves distant metastasis which can not be effectively treated with either surgery or radiation. Thus, patients with prostate cancer are likely to benefit if prostatectomy or radiotherapy is supplemented with chemotherapy using agents that kill residual prostate cancer cells or inhibit their growth, invasion and metastasis. One such agent is a soybean-derived serine protease inhibitor known as the Bowman-Birk Inhibitor (BBI).

BBI is a potent anticarcinogenic protease inhibitor that has been shown to inhibit the malignant transformation of cells in many tissue culture systems (Kennedy, A R, *Protease Inhibitors As Cancer Chemopreventive Agents*, Kennedy and Troll, Eds, Plenum Press, New York, 1993, p. 65–91). Extensive work has also demonstrated that BBI can suppress tumor development and reduce the cancer incidence in several species of animals treated with chemical carcinogens or radiation (Kennedy A R, *Protease Inhibitors As Cancer Chemopreventive Agents*, Kennedy and Troll, Eds, Plenum Press, New York, 1993, p. 9–46). Preliminary studies have indicated that BBI can either kill human prostate cancer cells or inhibit their growth.

Figure 1:
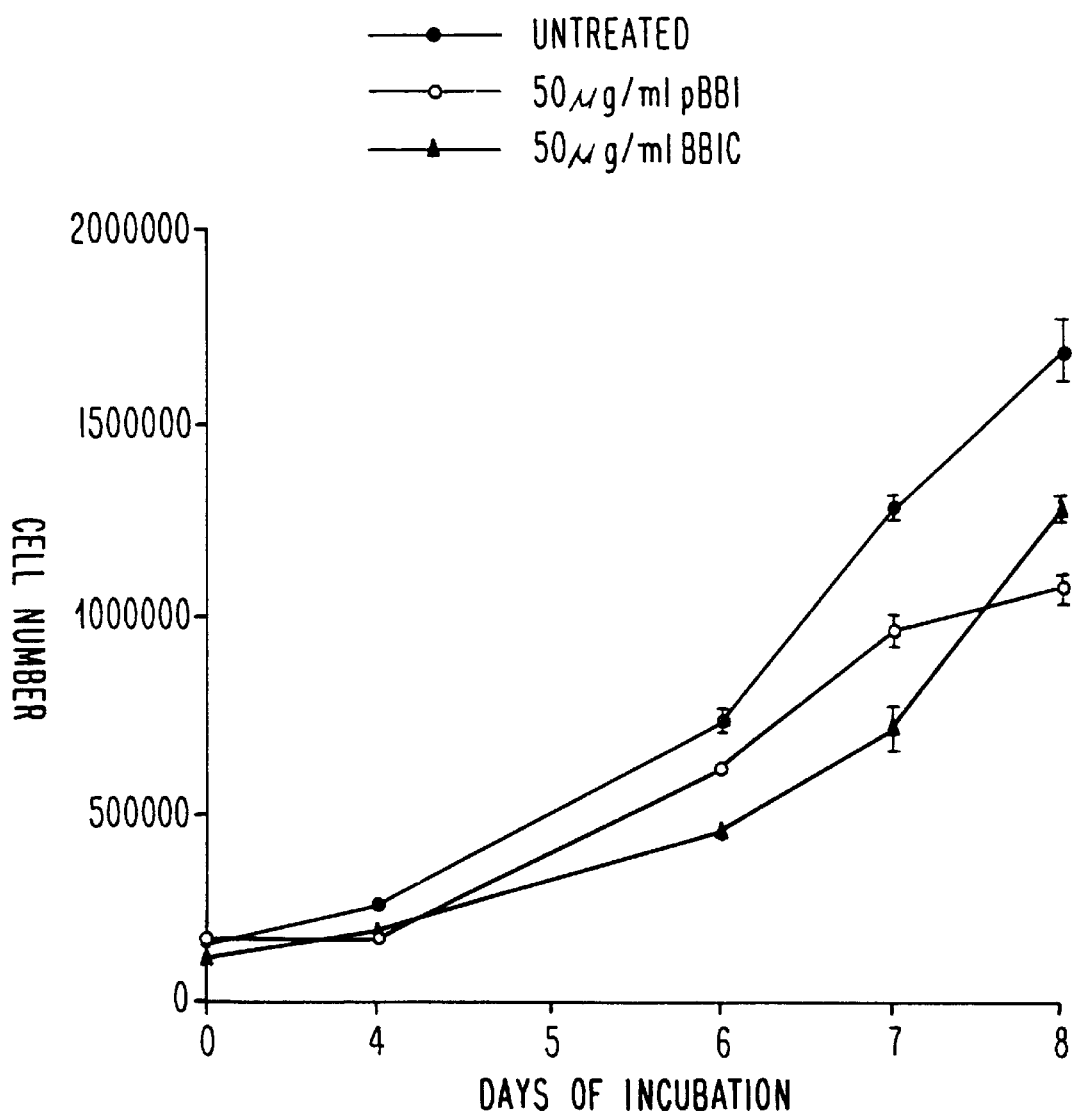
FIG. 1 shows the growth curves of LNCaP cells cultured in medium containing pBBI or Bowman-Birk Inhibitor concentrate (BBIC). LNCaP cells were plated into 60 mm tissue culture dishes and incubated for 8 days in control medium or media containing pBBI or BBIC at 50 μg/ml. Three dishes of cells from each group were treated with trypsin and counted with a Coulter counter every 24 hours during the incubation period (except day 5). Each data point represents the average of at least two independent experiments (Mean±S.E.).

The effect of BBI on the growth and survival of prostate cancer cells has been demonstrated using LNCaP cells. These cells were originally derived from a lymph node of a 50-year old Caucasian male with a confirmed diagnosis of metastatic prostate adenocarcinoma. The results of these experiments are summarized in FIG. 1, which shows that the inclusion of BBI in the culture medium significantly reduced the rate of growth of prostate cancer cells as compared to control cultures. Purified BBI (pBBI) and a BBI-enriched soybean preparation known as BBI Concentrate (BBIC) were utilized and both reduced the rate of growth of prostate cancer cells to a similar degree. Such an effect of pBBI and BBIC can result from either growth inhibition or cytotoxicity, or a combination of both of these mechanisms.

There is evidence that BBIC given as dietary supplement will have effects on human prostate cancer in vivo, as well as other diseases of the pelvic region. BBIC has been developed as a cancer preventive agent and is currently being evaluated in human trials. BBI has also been found to have anti-inflammatory activity. The experience of one patient treated with BBIC suggests that BBI is likely to have major effects on the symptoms of diseases/abnormal conditions of organs in the genitourinary tract/pelvic region which could be due to the anti-inflammatory activity of BBI or the ability of BBI to regulate smooth muscle contractions and, presumably, the ability of BBI to destroy the atypical prostate cells occurring in benign prostatic hyperplasia and/or prostate cancer. During two twelve day periods of BBIC treatment, the patient noted improvement in urinary symptoms which were assumed to be due to benign prostatic hyperplasia (BPH). His symptoms reverted to baseline when the BBIC therapy was discontinued. During the BBIC therapy, the patient also noted improvement in pre-existing symptoms of sexual dysfunction. Specifically, his ability to achieve and maintain erection returned to normal while on BBI.

Figure 2:
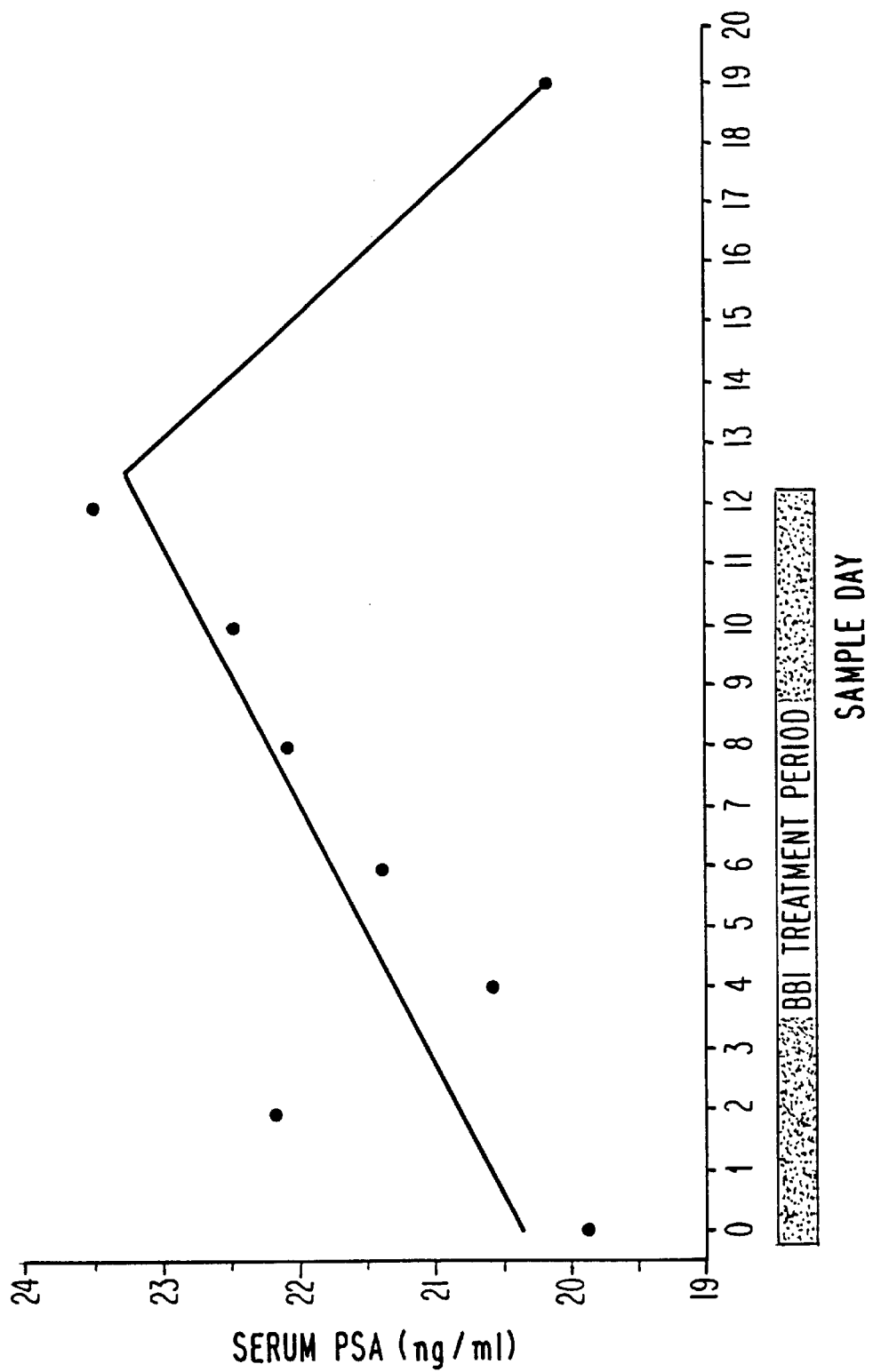
FIG. 2 shows the time course of serum PSA concentration in a BPH and prostate cancer patient after BBI administration. The patient ingested a soybean preparation (BBIC) containing 100 chymotrypsin inhibition units daily for a total of 12 days. The serum PSA level was measured by the standard PSA immunoassay using the Hybritech tandem-E kit.

As is usually the case with BPH, this patient had an abnormally high serum level of prostate specific antigen (PSA). The treatment with BBIC at a dose of 100 Chymotrypsin Inhibitor (C.I.) units per day for a twelve day period resulted in an approximately linear dose response relationship for PSA vs. days of BBIC therapy over the twelve days in which BBIC was taken, with the PSA going down to the normal "high" level for this patient when BBI was withdrawn, as shown in FIG. 2. For this patient, treatment with BBIC resulted in almost immediate relief of urinary symptoms. This patient was later diagnosed as having prostate cancer, which was presumably present at the time of BBIC therapy. Thus, the resulting changes in PSA levels could reflect a cell killing effect of BBI on prostate cancer cells. The curve shown in FIG. 2 is much like that observed in the treatment of prostate cancer by radiation. Radiation is known to kill the epithelial cells involved in prostate cancer, which results in higher serum levels of PSA as the prostate cancer cells disintegrate and spill their PSA contents into the blood. Alternatively, the observations related to elevated serum PSA levels with BBI therapy could have been due to cell killing effects of BBI on the atypical prostate cells present in BPH.

Figure 3:
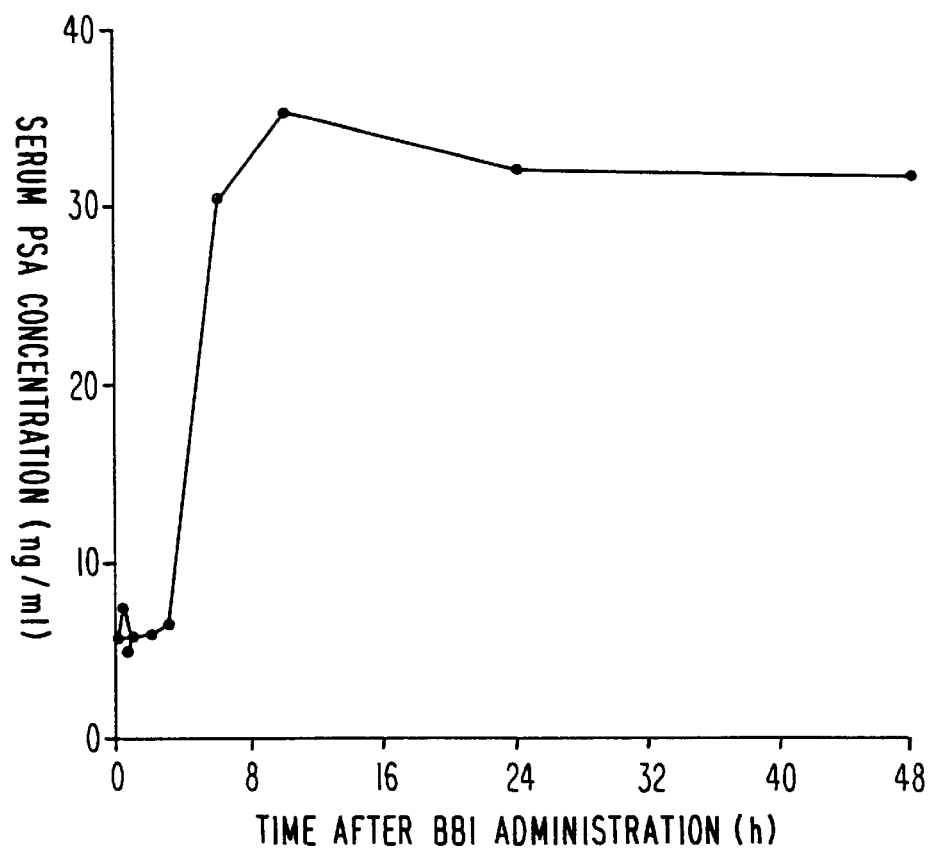
FIG. 3 shows the time course of serum PSA concentration in a patient with oral leukoplakia after BBIC administration. The patient ingested a single dose of BBIC containing 400 C.I. units. The serum PSA concentration was measured with a double-antibody sandwich ELISA using purified human PSA as a standard.

Another individual whose serum PSA levels were altered by BBI administration is a patient with oral leukoplakia. For this patient, who had a higher than normal serum PSA concentration prior to entering the study, there was a highly significant elevation in his serum PSA level after BBIC administration, as shown in FIG. 3. PSA is a serine protease that is produced exclusively by prostate epithelial cells. PSA is present in semen as a major protein component. Although in normal adult males the concentration of PSA can be as high as 0.7 mg per ml in seminal fluid, the serum PSA level is only about one millionth of that concentration. The large difference in PSA concentrations between semen and serum suggests that PSA normally does not enter the bloodstream at a relatively high level unless there is destruction of prostate cells which results in the release of PSA directly from the broken prostate cells into the bloodstream. This is supported by observations that many conditions damaging to prostate tissue, such as prostate cancer, benign prostatic hyperplasia (BPH), prostate inflammation (prostatitis) and mechanical pressure on the prostate gland, can all cause the serum PSA concentration to rise. It is assumed that the increase in serum PSA levels shown in FIG. 2 in the BPH prostate cancer patient after BBIC administration is an indication that BBI destroyed prostate cancer cells, or the atypical prostate cells occurring in BPH, which released PSA into the bloodstream. The sharp increase in serum PSA levels in the oral leukoplakia patient after BBIC administration suggests that BBIC treatment resulted in prostate cell death and the release of PSA into the bloodstream. While treatment with BBIC led to an increase in the serum PSA levels in the patient who had an elevated serum PSA level prior to BBIC administration, BBIC treatment did not affect the serum PSA levels in any of the human subjects whose serum PSA levels were normal (<4.0 ng/ml) prior to entering the BBIC oral cancer chemoprevention trial. The differential effect of BBI on serum PSA levels in people with normal and abnormal serum PSA levels suggests that BBI may selectively attack prostate cells involved in diseases such as prostate cancer and BPH, while leaving normal prostate cells intact. It is believed that the oral leukoplakia patient in the BBIC oral cancer prevention trial has an undiagnosed case of BPH or prostate cancer, in which atypical prostate cells would be present and affected by BBIC treatment. BBI can kill prostate cancer cells and possibly inhibit the growth of prostate cancer cells as well. Both of these effects should benefit patients with prostate cancer if BBIC is included as a supplement to surgery or radiation therapy.

The time course of changes in the serum concentration of PSA shown in both FIGS. 2 and 3 suggests that either an anti-inflammatory effect of BBI an effect of BBI on smooth muscle is responsible for the observed effects. An effect of BBI on smooth muscle is highly likely. The prostate gland surrounds the urethra, which is a tube that drains urine from the bladder. While BPH is an enlargement of prostate tissue, the symptoms of BPH can also be caused by an increase in the tightness of smooth muscle surrounding the bladder/urethra. When the muscle tightens, it squeezes the urethra and slows the rate at which urine can flow through the urethra, causing the urinary symptoms associated with BPH. It is thought that BBI may well be affecting the urinary symptoms associated with BPH "immediately" by its ability to control smooth muscle contractions. It is now believed that BBI may take the place of an important regulatory enzyme in the body, $\alpha$-1-antichymotrypsin. The chymotrypsin inhibitory activity of BBI is very similar to that of $\alpha$-1-antichymotrypsin. $\alpha$-1-antichymotrypsin is thought to play a regulatory role in smooth muscle contractions. By relaxing the muscle surrounding the urethra, urine would flow more easily and relieve the urinary symptoms associated with BPH (urinary symptoms commonly referred to as "urgency and frequency" problems). Similarly, a BBI effect on vascular smooth muscle could have an effect on symptoms of male sexual dysfunction. The fact that the patient with BPH and prostate cancer felt relief of urinary symptoms, as well as those symptoms associated with male sexual dysfunction, within hours after beginning BBIC therapy, and the fact that the patient in the leukoplakia trial showed changes in the serum PSA levels within hours of BBIC therapy, suggests that a BBI effect on smooth muscle is a more likely explanation for the BBI effect on symptoms of pelvic disease than is a BBI cell killing effect on atypical prostate cells. A BBI effect leading to the relaxation of smooth muscles would be expected to occur very soon after BBI ingestion. BBI appears in the blood soon after ingestion of BBI, with biological effects, such as changes in levels of proteolytic activities in the oral buccal mucosal cells of patients with oral leukoplakia, occurring as early as 6 hours after BBI therapy. This suggests that BBI treatment has resulted in the opening of a constricted urethra which has perhaps led to the destruction of atypical prostate cells and resultant increased serum PSA levels. An effect of BBI related to smooth muscle/urination difficulties would apply to female patients as well. Female patients also have difficulty with "frequency and urgency" of urination due to problems with the smooth muscle surrounding the urethra/bladder.

In the present invention, compositions comprising BBI for the treatment of diseases or atypical conditions in the pelvis are provided. In a preferred embodiment, these compositions further comprise a pharmaceutically acceptable carrier. By "BBI" it is meant to include any Bowman-Birk Inhibitor or Bowman-Birk Inhibitor product, including, but not limited to, BBI prepared by methods known in the art and BBI concentrates prepared in accordance with the method of U.S. Pat. No. 5,217,717. Also provided are methods of treating prostate disease in an animal by administering an effective amount of a composition comprising BBI. By "animal" it is meant to include, but is not limited to, any mammal including humans.

Administration of an effective amount of the claimed compositions, either as a prophylactic dietary supplement or a pharmaceutical, is within the teachings of the invention. The term "effective amount" refers to an amount which alters the expression of certain types of proteolytic activities. Such an amount can be determined by those of skill in the art in accordance with known methods. For example, based on information presented in FIGS. 1–3, BBIC doses in the range of 200–4000 mg/day would be effective in humans [50–100 µg/ml×4000 ml (average blood volume in man)= 200–400 mg BBIC; 100–400 CI units of BBIC is equivalent to 1000–4000 mg BBIC, as described in Kennedy, *Prevent. Med.* 1993, 22, 796–811, pp. 797]. Further, based on data from the published literature, doses of purified BBI as low as 1.3 mg/day (in rats) and more than 150 mg/day are effective in animal models of carcinogenesis (St. Clair et al., *Cancer Res.* 1990, 50, 580–586; Kennedy, *J. Nutr.* 1995, 125, 733S–743S; van Hofe et al., *Carcinogenesis* 1991, 12, 2147–2150). Doses lower than 1 mg/day to rats are likely to be effective as well (Kennedy, *J. Nutr.* 1995, supra), with doses of as little as 0.001 µg/ml showing activity in vitro to suppress transformation of irradiated cells (Yavelow et al., *Proc. Natl. Acad. Sci.* 1985, 82-5395–5399). These in vitro results would suggest that doses considerably lower than human doses of 200 mg BBIC per day would be effective in the prevention of cancer. Compositions of the present invention may be administered parenterally, rectally, topically, transdermally or orally, preferably orally. Published studies have shown that BBI is effective following a variety of routes of administration, including oral dosing (Kennedy, *J. Nutr.* 1995, 125, 733S–743S; Evans et al., *Radiat. Res.* 1992, 132, 259–262). Examples of pharmaceutical or prophylactic dietary supplement formulations include, but are not limited to, syrups, suspensions, emulsions, tablets, capsules, lozenges and mouthwashes.

One embodiment of the invention is a liquid formulation comprising a suspension or solution of the composition in a pharmaceutically acceptable liquid carrier. Suitable liquid carriers include, but are not limited to, ethanol, glycerin, non-aqueous solvents such as polyethylene glycols, oils or water with a suspending agent, preservatives, flavorings or coloring agents, or any suitable combination thereof.

In another embodiment, a composition in the form of a tablet is prepared using any suitable pharmaceutical carrier routinely used for preparing solid formulations. Examples of such carriers include, but are not limited to, magnesium stearate, starch, lactose, sucrose and cellulose.

Compositions in the form of capsules are prepared using routine encapsulating procedure. For example, pellets, granules or powder containing a composition of the instant invention can be prepared using standard carriers and then filled into a hard gelatin capsule. Alternatively, a dispersion or suspension can be prepared using any suitable pharmaceutical carrier(s) and the dispersion or suspension is then filled into a soft gelatin capsule. Suitable pharmaceutical carriers include, but are not limited to, aqueous gums, cellulose, silicates and oils.

In yet another embodiment, a composition for parenteral administration is formulated as a solution or suspension. This solution or suspension will generally include the composition of the instant invention in a sterile aqueous carrier or parenterally acceptable oil. Examples of parenterally acceptable oils include, but are not limited to, polyethylene glycol, polyvinyl pyrrolidone, lecithin, arachis oils and sesame oil. Alternatively, the solution can be lyophilized and then reconstituted with a suitable solvent just prior to administration.

The following examples illustrate the practice of this invention and the characterization and utility of products resulting therefrom. They are provided for illustrative purposes only and are not intended to limit the invention.

EXAMPLES

Two metastatic human prostate cancer cell lines known as LNCaP and PC-3 cells were used in the studies. LNCaP cells were derived from a metastatic lesion in a lymph node of a 50-year-old Caucasian male patient with a confirmed diagnosis of metastatic prostate carcinoma (Horoszewicz et al., *Cancer Res.* 1983, 43, 1809–1818; Gibas et al., *Cancer Genet. Cytogen.* 1984, 11, 399–404). PC-3 cells were derived from a 62-year-old male Caucasian patient with grade IV prostatic adenocarcinoma that is metastatic in both the patient and in nude mice (Kaighn et al., *Invest. Urol.* 1979, 17, 16–23; Ohnuki et al., *Cancer Res.* 1989, 40, 524–534). These two cell lines represent different stages of advanced prostate cancer and are good models for studies of advanced human prostate cancer. To determine whether BBI causes growth inhibition in these cell lines, a $^3$H-thymidine incorporation assay is performed in accordance with well known methods (Samid et al., *J. Clin Invest.* 1993, 91, 2288–2295). LNCaP and PC-3 cells are cultured in control medium or medium containing 50 µg/ml of pBBI or BBIC and incubated with 1 µCi/ml of $^3$H-thymidine (DuPond-NEM) for 2 hours. After incubation, the cells are washed with PBS, harvested with cell scrapers and precipitated with ice-cold 5% trichloroacetic acid (TCA) . The TCA-precipitable radioactivity is quantitated with a liquid scintillation counter to measure the rate of $^3$H-thymidine incorporation. A decrease in the $^3$H-thymidine incorporation rate in the cells cultured in the medium containing BBI or BBIC indicates that pBBI or BBIC inhibits the growth of prostate cancer cells by suppressing DNA synthesis.

The effect of BBI on the growth of prostate cancer cells is determined by a cell cycling assay which is known in the art (Vindelov and Christensen, *Cytometry* 1990, 11, 753–770). To perform the experiments, LNCaP and PC-3 cells will be cultured in control medium or medium containing 50 µg/ml pBBI or BBIC for 48 to 72 hours, then trypsinized and stained with propidium iodide. The cytometric analysis will be performed on a Becton-Dickinson FACScan flow cytometer within two hours of staining. Red fluorescence will be detected through a 585 nm bandpass filter with a bandwidth of 42 nm. Ten thousand events will be collected for each sample and data will be analyzed based on manual gates placed according to the G1 and G2/M peak positions in concurrently stained unsynchronized cells. An abnormal accumulation of the cells in any particular phase of the cell cycle would indicate that pBBI or BBIC inhibits growth of prostate cancer cells by blocking the cycling of these cells.

The effect of BBI on the survival of prostate cancer cells is assessed by a trypan blue exclusion assay and the lactate dehydrogenase (LDH) and PSA release assays. To perform the LDH release assay, LNCaP and PC-3 cells are cultured in control medium or medium containing 50 μg/ml of BBI or BBIC for 48 to 72 hours, then washed with PBS and incubated for 3 to 6 hours in serum-free medium (serum contains LDH which interfere with the assay) in the presence or absence of BBI. The LDH activity in the conditioned media is determined using an LDH diagnostic Kit (Sigma Chemical Company). Since LNCaP is a cell line known to produce PSA, the medium conditioned with LNCaP cells is also analyzed by PSA immunoassay to determine the PSA concentration in the medium. An increase in the level of LDH or PSA in the medium conditioned with the prostate cancer cells cultured in the presence of BBI indicates a BBI-induced cell killing effect which causes intracellular LDH and PSA to be released into the medium. If a significantly higher level of cell death is detected by a trypan blue exclusion assay or LDH and PSA release assays in the prostate cancer cells treated with pBBI or BBIC, further experiments are performed to determine whether BBI induces cell killing through apoptosis.

Apoptosis in the prostate cancer cells cultured in medium with or without BBI is measured primarily by propidium iodide (PI) staining and terminal deoxynucleotide transferase labeling of fragmented DNA in situ. The PI staining is performed as described by Muschel et al., *Cancer Res.* 1995, 55, 995–998. In these studies, cells are be examined for evidence of fragmented nuclei with regions of hyperchromatic staining by PI. The terminal deoxynucleotide transferase labeling is carried out using the Apoptag kit (Oncor) according to the manufacturer's instructions. This method detects apoptosis through labeling of the 3' hydroxy terminus of nuclease-cleaved DNA. The cells stained by PI or labeled using the Apoptag kit are examined under a fluorescent microscope. An increase in the incidence of apoptosis in the prostate cancer cells treated with pBBI or BBIC is evidence that BBI causes the death of prostate cancer cells by inducing apoptosis.

The effect of BBI on the growth of human prostate cancer cells is determined in BALB/c nude mice according to procedures known in the art (Horoszewicz et al., *Cancer Res.* 1983, 43, 1809–1818; Ware et al., *J. Urol.* 1982, 128, 1064–1067). Forty nude mice are divided into four groups of 10 mice per group. Two groups are maintained on a control diet, while the other two groups are fed with a diet containing 1% BBIC. Four days after the mice are introduced onto the appropriate diets, one group of mice on each diet is subcutaneously inoculated with LNCaP or PC-3 cells ($4 \times 10^6$ cells per mouse). After inoculation, the mice are fed on the same diets that they were fed prior to the inoculation and observed for 60 days. Upon death (if death occurs prior to the end of the experiment) or upon sacrifice at the end of the 60-day experimental period, autopsies are performed to count tumor numbers and measure the size of tumors. The data obtained from the groups maintained on the BBIC-containing diet are compared with that from the control groups to determine whether BBIC inhibits the growth and/or metastasis of human prostate cancer cells in nude mice.

What is claimed is:

1. A method for increasing urine flow and treating male erectile dysfunction in a patient with benign prostatic hyperplasia and/or adenocarcinoma of the prostate comprising administering to the patient an amount of Bowman Birk Inhibitor effective to increase urine flow and treat male erectile dysfunction.

* * * * *